(12) United States Patent
Abehasera

(10) Patent No.: US 11,053,040 B1
(45) Date of Patent: Jul. 6, 2021

(54) CONTAINER WITH INTEGRATED SCALE

(71) Applicant: TRI Innovations, LLC, Hallandale Beach, FL (US)

(72) Inventor: Benyamin Abehasera, Hallandale Beach, FL (US)

(73) Assignee: TRI Innovations, LLC, Hallandale Beach, FL (US)

( * ) Notice: Subject to any disclaimer, the term of this patent is extended or adjusted under 35 U.S.C. 154(b) by 0 days.

(21) Appl. No.: 17/033,062

(22) Filed: Sep. 25, 2020

(51) Int. Cl.
| | |
|---|---|
| *A61L 2/10* | (2006.01) |
| *G01G 19/52* | (2006.01) |
| *G01G 19/14* | (2006.01) |
| *B65D 41/04* | (2006.01) |
| *B65B 55/08* | (2006.01) |
| *A61L 9/00* | (2006.01) |
| *F21Y 115/10* | (2016.01) |

(52) U.S. Cl.
CPC .............. *B65B 55/08* (2013.01); *A61L 9/00* (2013.01); *F21Y 2115/10* (2016.08)

(58) Field of Classification Search
CPC ........ G01G 19/52; G01G 19/14; B65D 41/04; A61L 2/10; B65B 55/08
See application file for complete search history.

(56) References Cited

U.S. PATENT DOCUMENTS

| | | | | |
|---|---|---|---|---|
| 9,981,790 | B1* | 5/2018 | Ost | G01G 19/52 |
| 2011/0241828 | A1* | 10/2011 | Wang | B65D 41/04 |
| | | | | 340/5.53 |
| 2014/0360374 | A1* | 12/2014 | Hatfield | B01D 53/0415 |
| | | | | 96/108 |
| 2018/0037383 | A1* | 2/2018 | Kneer | B65D 51/20 |
| 2019/0038008 | A1* | 2/2019 | Lee | B65D 51/28 |
| 2020/0270034 | A1* | 8/2020 | Guduru | C02F 1/002 |

* cited by examiner

*Primary Examiner* — Kevin Joyner
(74) *Attorney, Agent, or Firm* — Berger Singerman LLP; Geoffrey Lottenberg

(57) ABSTRACT

A container and cap stores and measures material. A container has a cap removably attached to a double-walled container section. The cap has a housing between a base and a scale tray. The housing contains electronic components including a display, microcontroller, a sensor array and functional buttons. The scale tray includes a ring of LEDs that direct into the container section to sanitize and illuminate. The sensor array of the cap includes a scale transducer and humidity and temperature sensors. The container can be flipped over so the base on an underlying surface and so that the material the container falls down onto the scale tray, so the contents can be weighed. The cap can be removed and used as a stand-alone scale. The functions of the electronics can be controlled by an external devices, like a smartphone, through a software application.

11 Claims, 4 Drawing Sheets

CONTAINER WITH INTEGRATED SCALE

CROSS REFERENCE TO RELATED APPLICATIONS

N/A

FIELD OF THE INVENTION

The present invention relates to the technical field of containers, more particularly to a computer-connectable container with an integrated scale for storing herbs and other materials.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" or "in some embodiments" in various places throughout this specification are not necessarily all referring to the same embodiment. Furthermore, the particular features, structures or characteristics may be combined in any suitable manner in one or more embodiments.

Figure 1:
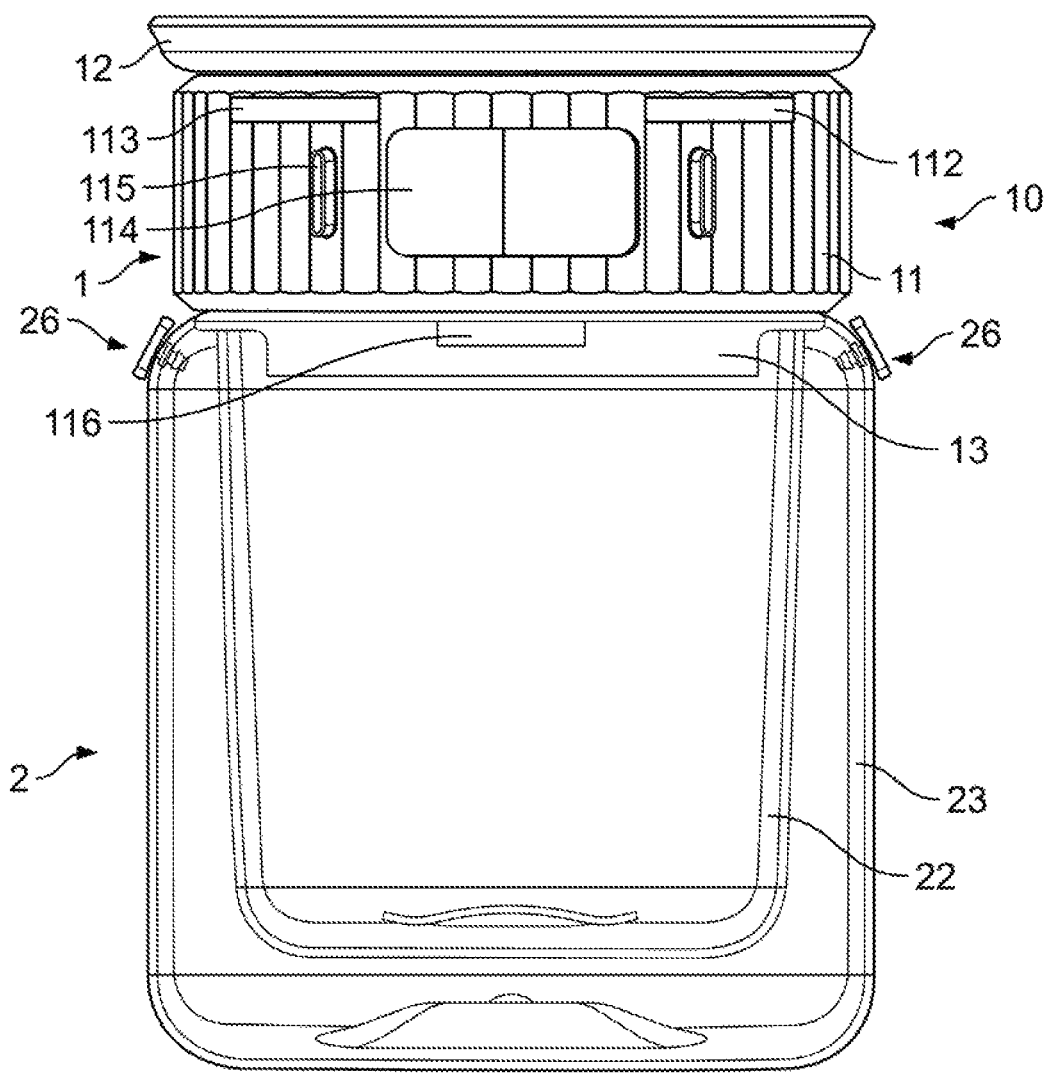
FIG. 1 is a perspective view of the container.
Figure 2:
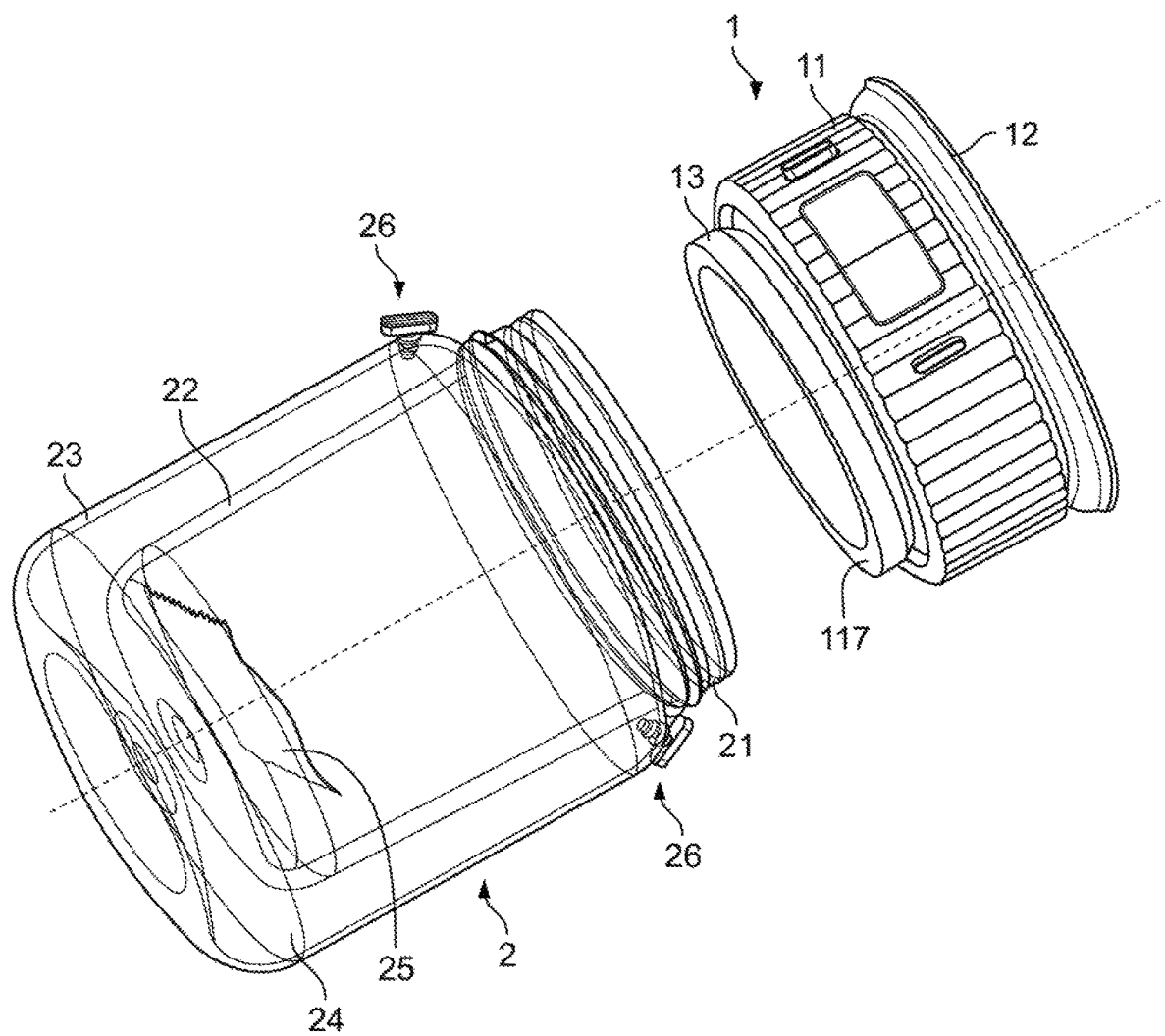
FIG. 2 is exploded view of the container.

Referring to FIGS. 1 and 2, the multi-function container 10 of the present invention comprises a multi-function cap 1 and a container section 2. Cap 1 includes a housing 11 disposed between a base 12 and a scale tray 13. In some embodiments, the cap 1 is removably attached to the container 2 by snap-fit, interference fit, threads, magnetic connection, or the like for ease of use, cleaning, and replacement of parts. The container 10 is designed to store material in container section 2, which is then covered and sealed by the cap 1.

The cap 1 provides numerous functions including scale functionality. Accordingly, in some use cases the container 10 is oriented such that the base 12 rests on an underlying surface and scale tray 13 is oriented upward such that contents the container section 2 fall downward onto the scale tray 13 so that the contents can be weighed without removing the cap 1 from the container section 2. In other use cases, the cap 1 can be removed from the container 1 and flipped over such that the base 12 rests on an underlying surface and scale tray 13 faces upward to be used an "open" scale to weigh any material desired (whether stored in the container section 2, or otherwise). In this way, the cap 1 can be used independently of the container section 2 for any or all of the functions that cap 1 may provide as described herein.

In some embodiments, the housing 11 includes a power source, such as a battery 111 (See FIG. 4B) or external power supply, a microcontroller 112, a communications device 113, a display 114, one or more buttons 115, and a sensor array 116. The microcontroller 112 provides power and communication connectivity for the various system components including the communications device 113, display 114, and sensor array 116. In some embodiments the microcontroller 112 comprises a processor (CPU), memory, and control programming for the various input and output peripherals. The communications device 113 may comprise a modem, Wifi chip, a Bluetooth chip, a NFC chip, a Universal Serial Bus (USB) port, or combinations thereof. In some embodiments the communication device 113 is configured to communicate with an external computing device such as a computer or smartphone in order to send and receive data including status information, scale information, and commands. Such data transmission can be accomplished through a customized application running on the smartphone or computer.

The display 114 may comprise an LED, LCD, OLED, or like display that can be used to output various information including contents weight, battery status, communications status, and the like. The buttons 115 are used an onboard control interface and may be multi-function and programmed to operate different functions based on the number and duration of presses. In some embodiments one or more of the buttons 115 is a multi-touch touch screen for added functionality.

The sensor array 116 can comprise a multifunction sensor system to interact with the scale tray 13 and/or to detect and transmit information about the conditions inside the container section 2. In some embodiments, the sensor array 116 is functions as a scale transducer and is in physical communication with the scale tray 13 to measure the mechanical energy, i.e. the pressure applied to the scale tray 13 by the contents placed thereon, and converts the pressure to an electrical output (e.g. current or voltage differential). In some embodiments, the sensor array 116 can detect the temperature and/or humidity of the contents of the container 2. The electrical output at the sensor 116 is processed into a digital signal by the microcontroller 112 which digital signal can then be outputted on display 114 or through the communications device 113.

In some embodiments, the cap 1 includes safety and locking features that function by way of the various system components. For example, the display 114 includes a fingerprint reader or other biometric lock system that is configurable via the customized application. In some embodiments, the communications device 113 can function as a locking system such as, for example, a proximity-base locking system via NFC or Bluetooth.

In some embodiments, cap 1 is structured such that the scale tray 13 forms an air-tight seal with the top of the container section 2 when the cap 1 is closed. Accordingly, in some embodiments the perimeter of the scale tray 13 may include a sealing elements such as a rubber grommet to facilitate a tight seal. In some embodiments, the container section 2 may include a threaded neck 21 which engages corresponding threads on the cap 1, for example such threads disposed at an interior surface of the housing 11, adjacent to the scale tray 13. In some embodiments, the threaded neck 21 may be configured as "child proof" threads as shown in FIG. 3 in order to prevent accidental opening.

In some embodiments, container section 2 may comprise an inner container 22 and an outer container 23. There may be a space or gap 24 between inner and outer containers 22 and 23 which can function to provide insulation for the contents inside inner container 22 to promote preservations and freshness of the contents. In some embodiments, one or more resealable apertures 26 are disposed through the wall of the outer container so that air pressure can be relieved. The apertures 26 may be resealable by a cork, rubber stopper, grommet, foil seal, sealing cap, or the like. In some embodiments, liquids, gels, or gases can be introduced into the gap 24 through the apertures 26 such as, for example, hot or cold water, cleaning agents, insulating agents, or the like. In some embodiments, for example, colored water can be introduced into the gap 24 to provide unique aesthetics.

A removable additive 25, such as a desiccant, odor eliminator, air freshener, flavorant (i.e. flavoring agent), or colorant may be disposed inside the container 10, for example on the cap 1 or inside the inner container 22 and may be attachable to the bottom thereof, for example, by magnets or hook-and-loop fastener. In some embodiments, the additive 25 is liquid or gel ingredient that can emit flavorants and/or colorants that can change or enhance the flavor, odor, and/or color of the material stored in the container section 2. The additive 25 can be used in combination with the LED light source (described below) or electric current to activate or trigger release of the flavorants or colorants. In some embodiments, the additive 25 may be an exothermic or endothermic reactant that can be used to warm or cool in the ingredients in the container section 2.

Figure 3:
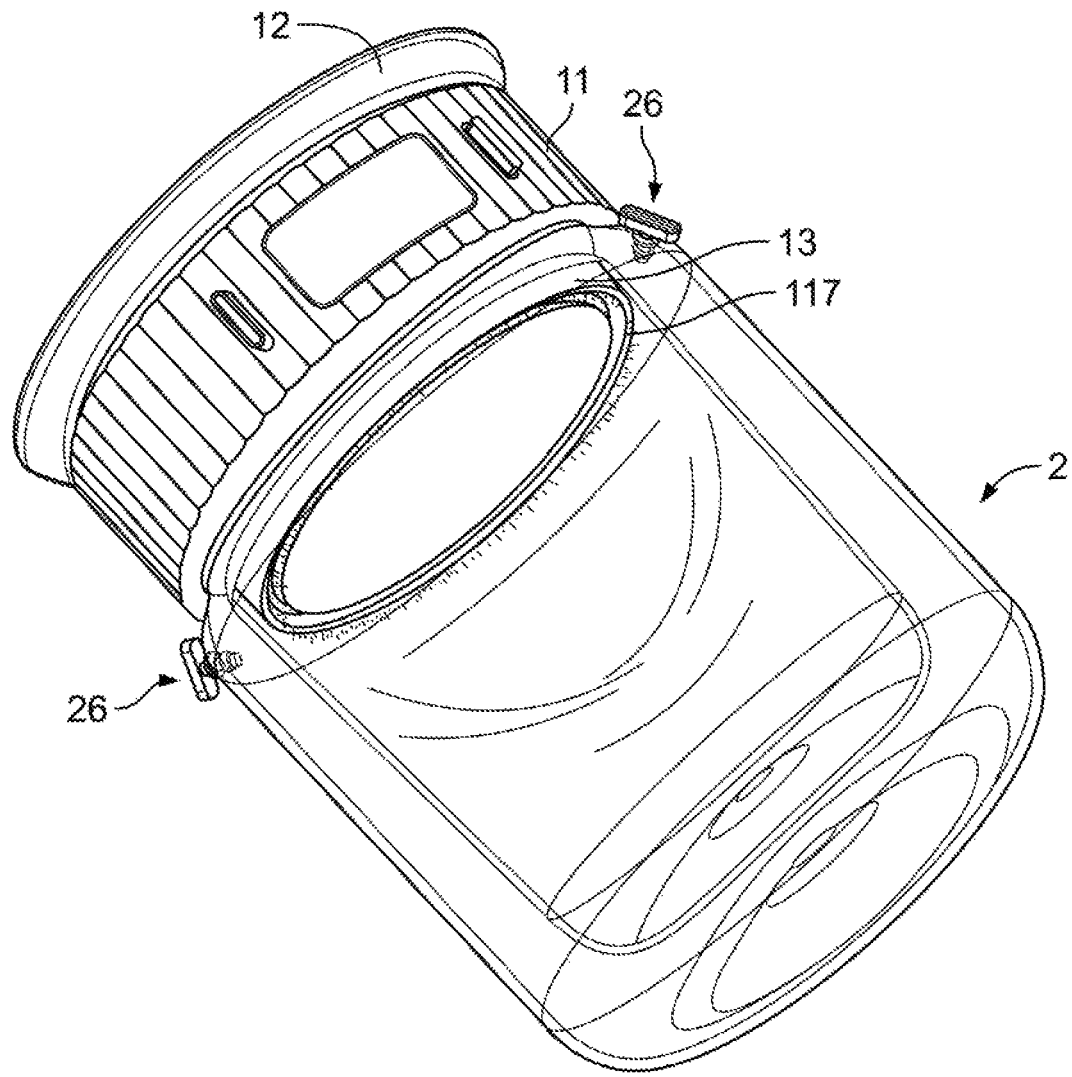
FIG. 3 is another perspective view of the container showing and LED feature.

With reference to FIG. 3, in some embodiments the cap 1 can further include a UV or LED light ring 117 or strip that, in some embodiments, is disposed at or about the scale tray 13. In some embodiments the light ring 117 is configured with one or more LEDs (light emitting diodes) configured to emit light in the UVC (100-280 nm) range in order to sanitize the container section 2 and its contents, or to sanitize any other areas or spaces should the cap 1 be used separate and independently of the container section 2. In some embodiments, the light ring 117 comprises one or more RGB LEDs, the color of which are user-selectable through the electronics of the cap 1. In Some embodiments, the LEDs are be configured to emit light a wavelength effective to activate the additive 25. The light ring 117 can be placed in electrical communication with the microcontroller 112 and, therefore, the communications device 113.

Figure 5:
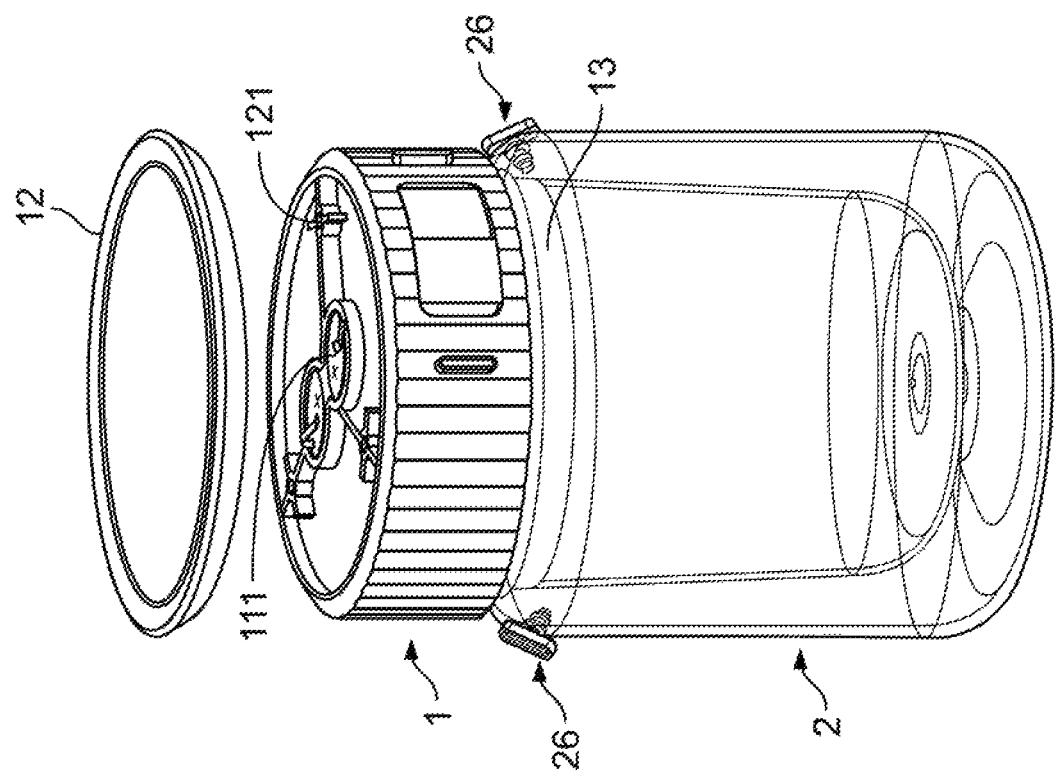
FIG. 5 is yet another exploded view of the container.
Figure 4:
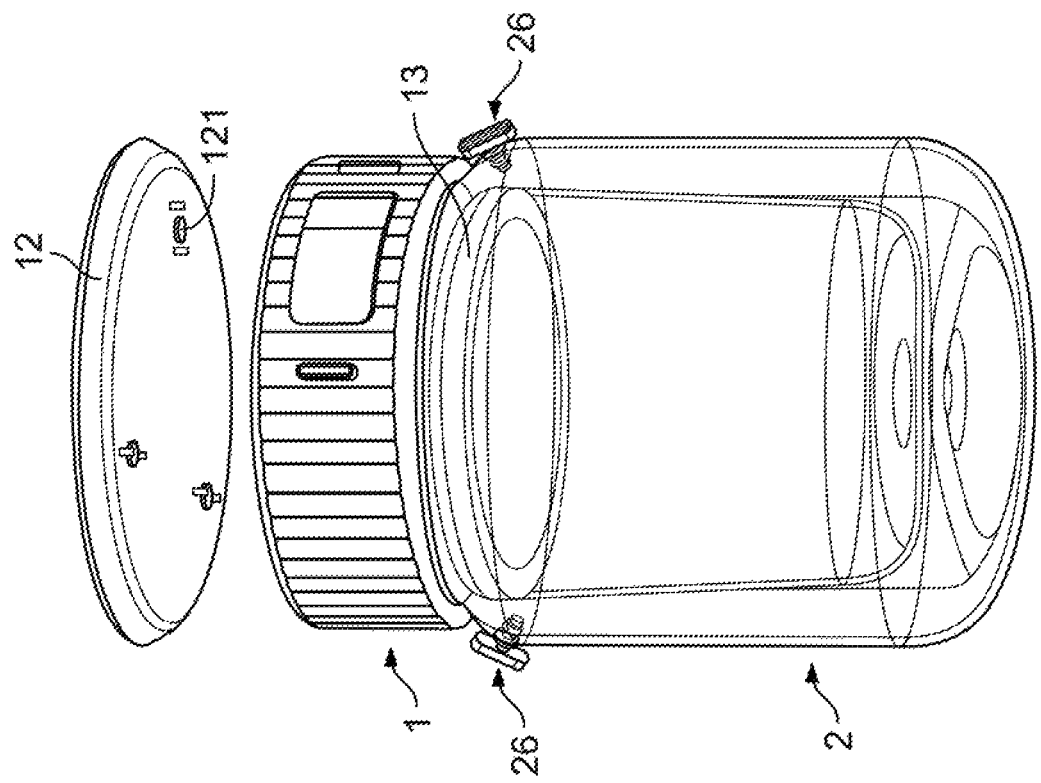
FIG. 4 is another exploded view of the container.

With reference to FIGS. 4 and 5, in some embodiments the base 12 is removable from the housing 11 in order to access the battery 111 to replace same. The base 12 can be removably attached to the housing by magnets 121 but other connections like snap-fit or interference-fit may be equally suitable.

The materials selected for the container 10 of the present invention are not particularly limiting; however, in some embodiments, at least a portion of container section 2 is comprised of a transparent material so that the user can easily observe the contents therein.

As noted above, the container includes connectivity features such that the communications device can communicate with an outboard smartphone or computer for added functionality. In some embodiments the container is "app-enabled" and works in conjunction with control and notification software. The user can utilize an application running on a smartphone or computer to obtain information from the container such as weight, battery status, or the like. In some embodiments, each time the container is turned on either or both of the scales obtains a weight measurements and stores corresponding weight data in the memory of the microcontroller. Then, each time of the user loads the application on his computing device, the stored weight information is automatically synchronized to the application. The container can also be configured to send outbound alerts to advise the user that, for example, the weight of product in the container section 2 has dropped below a predetermined level. The application may also include functionality to permit the user to directly purchase new products to be used in conjunction with the container.

It is appreciated and understood that the present invention provides an easy to use, feature-rich storage container for the storage, grinding, and management of herb such as tobacco, hemp, Chinese herbal medicine, spices etc. for smoking or other uses. Convenience features such as the integrated scales, display, onboard communications, transparent container, and various storage areas provide an "all-in-one" solution that addresses many wants and desires in the art.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:

1. A container, comprising:
   a cap removably attached to a container section;
   the cap including a housing disposed between a base and a scale tray;
   the cap including a microcontroller, a display, a sensor array, and a battery;
   wherein the sensor array comprises a scale transducer in electrical communication with the microcontroller and a temperature sensor, a humidity sensor, or combinations thereof;
   wherein the base is removable from the housing to access the battery;
   wherein the cap includes one or more UV sanitizing LEDs disposed in a ring around the scale tray, the UV sanitizing LEDs emitting light in the range of 200-280 nm;
   wherein the container is configured such that the base of the cap is disposed on an underlying surface, in order to weight contents of the container section on the scale tray.

2. The container of claim 1, wherein the display is in electrical communication with the microcontroller.

3. The container of claim 2, wherein the display includes a fingerprint scanner.

4. The container of claim 1, wherein the cap includes one or more buttons in electrical communication with the microcontroller.

5. The container of claim 1, wherein the cap includes a communications device comprising a modem, Wifi chip, a Bluetooth chip, a NFC chip, a Universal Serial Bus (USB) port, or combinations thereof.

6. The container of claim 5, wherein the communication device is configured to communicate with an external computing device in order to send and receive data including status information, scale information, temperature information, humidity information, and commands.

7. The container of claim 1, wherein the container section includes an inner container and an outer container with a gap disposed between the inner and outer containers.

8. The container of claim 7, including one or more resealable apertures in the outer container.

9. The container of claim 7, wherein the gap is configured to be filled with a liquid, gas, or gel.

10. The container of claim 1, including an additive comprising a desiccant, odor eliminator, flavorant, colorant, or combinations thereof.

11. The container of claim 1, wherein the cap is lockable on the container section by corresponding child proof threads.

* * * * *